United States Patent
Bruggeman et al.

[11] Patent Number: 6,142,693
[45] Date of Patent: Nov. 7, 2000

[54] LIQUID DISPENSER AND DISTRIBUTION APPARATUS FOR WASHING STRUCTURES, AND METHODS

[75] Inventors: Thomas W. Bruggeman, Forest Lake; Daniel J. Bruggeman, Minneapolis; Charles J. Lever, Andover; Stephen C. Kohs, Forest Lake, all of Minn.

[73] Assignee: Diversified Dynamics Corporation, Minneapolis, Minn.

[21] Appl. No.: 09/323,320

[22] Filed: Jun. 1, 1999

[51] Int. Cl.[7] .................................................... B43K 5/06
[52] U.S. Cl. ........................ 401/176; 401/272; 401/270; 401/261; 401/205; 15/147.2; 15/229.4; 15/228; 15/220.1
[58] Field of Search ...................... 401/176, 196, 401/205, 272, 282, 148, 170, 171, 270, 182, 261, 263, 6; 15/147.2, 209.1, 210.1, 229.4, 229.8, 228, 231, 232, 233, 220.1

[56] References Cited

U.S. PATENT DOCUMENTS

| | | | |
|---|---|---|---|
| 1,268,271 | 6/1918 | Nelson | 401/176 |
| 1,691,024 | 11/1928 | Gedge | 401/205 |
| 2,011,635 | 8/1935 | Homan | 401/148 |
| 2,082,582 | 6/1937 | Kling . | |
| 2,249,401 | 7/1941 | Sieg . | |
| 2,281,367 | 4/1942 | Moll | 401/272 |
| 2,521,967 | 9/1950 | Dean . | |
| 2,613,384 | 10/1952 | Collins . | |
| 2,682,071 | 6/1954 | Linderoth | 15/228 |
| 2,727,268 | 12/1955 | Hucke | 15/233 |
| 2,997,732 | 8/1961 | Gilchrist et al. . | |
| 3,148,401 | 9/1964 | Gilchrist et al. | 401/272 |
| 3,175,242 | 3/1965 | Kamondy et al. . | |
| 3,455,638 | 7/1969 | Braswell . | |
| 3,459,482 | 8/1969 | Fears . | |
| 3,783,469 | 1/1974 | Siemund . | |
| 3,837,747 | 9/1974 | Seymore . | |
| 4,032,239 | 6/1977 | Maupin | 15/228 |
| 4,312,093 | 1/1982 | Raab . | |
| 4,315,342 | 2/1982 | Ash . | |
| 4,475,262 | 10/1984 | Downer . | |
| 4,695,176 | 9/1987 | Simonette et al. . | |
| 4,732,503 | 3/1988 | Bader et al. . | |
| 4,810,123 | 3/1989 | Bruggeman . | |
| 4,822,194 | 4/1989 | Simonette . | |
| 4,944,623 | 7/1990 | McNeil . | |
| 4,971,471 | 11/1990 | Sloan . | |
| 4,997,302 | 3/1991 | Simonette . | |
| 5,425,589 | 6/1995 | Griffin et al. . | |

*Primary Examiner*—David J. Walczak
*Attorney, Agent, or Firm*—Merchant & Gould P.C.

[57] ABSTRACT

A liquid dispenser arrangement includes a self-contained pump and a discharge head. The pump has a liquid reservoir, while the discharge head has an applicator construction and an aperture. The aperture will be in liquid flow communication with the liquid reservoir. The discharge head is constructed and arranged to selectively take in liquid from an external liquid source through the aperture and convey the liquid to the liquid reservoir, when a pressure differential is established between the liquid reservoir and the external liquid source by the pump. The discharge head is also constructed and arranged to selectively eject liquid from the liquid reservoir through the aperture for distribution by the applicator construction. The applicator construction preferably includes a molded, flexible member with the aperture being in a portion of the flexible member. Methods of assembly and use are also disclosed.

18 Claims, 9 Drawing Sheets

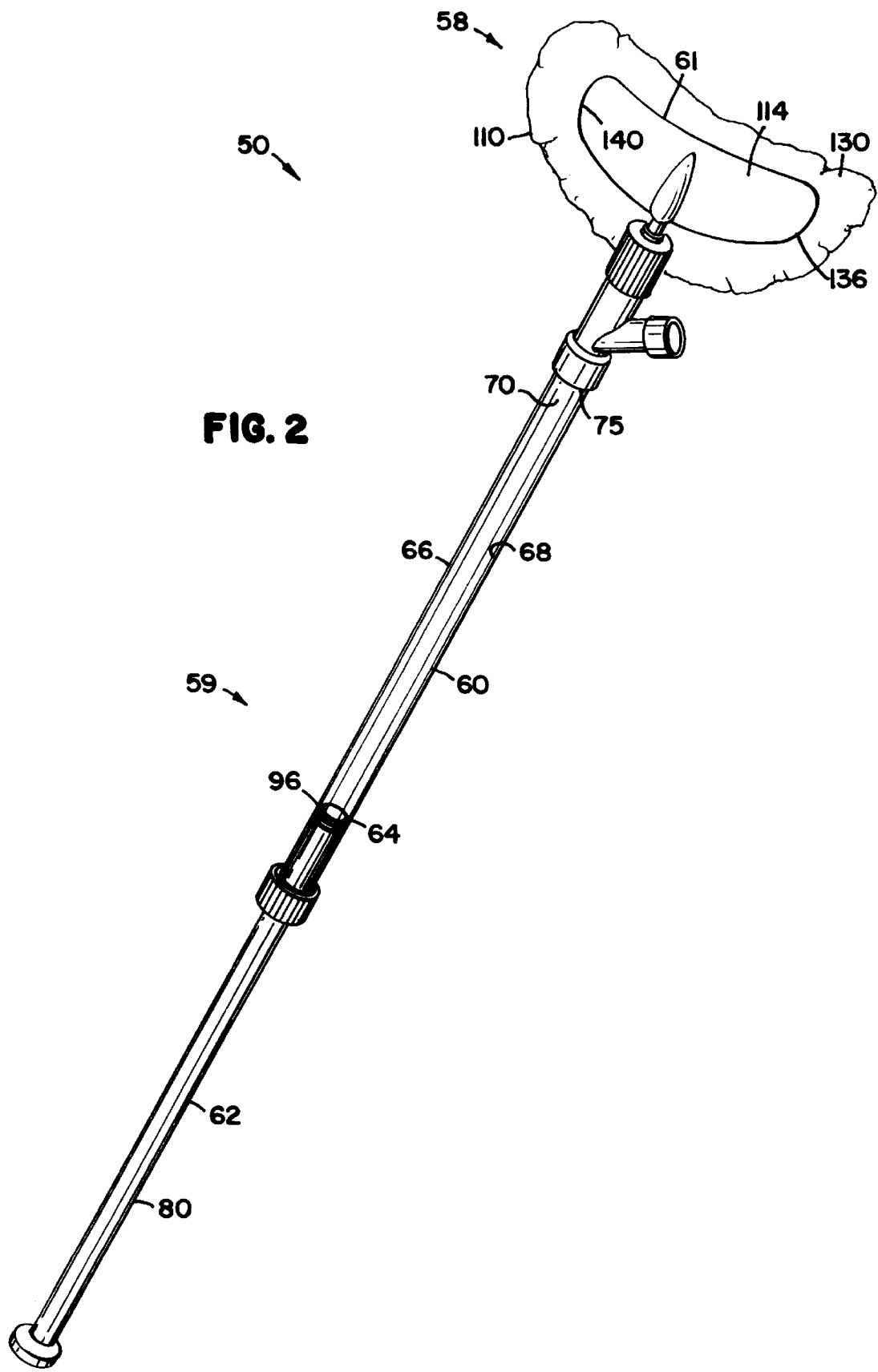

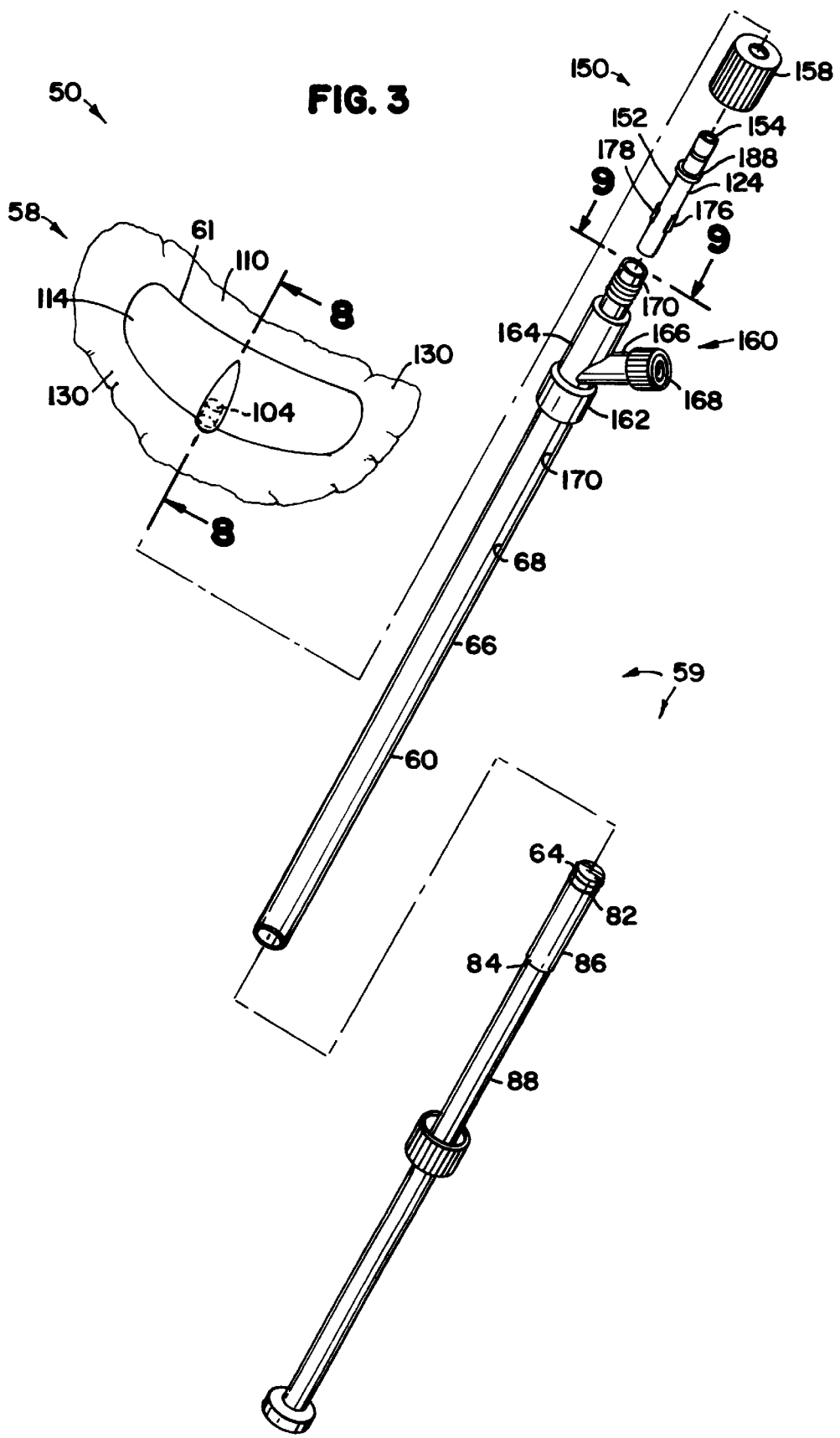

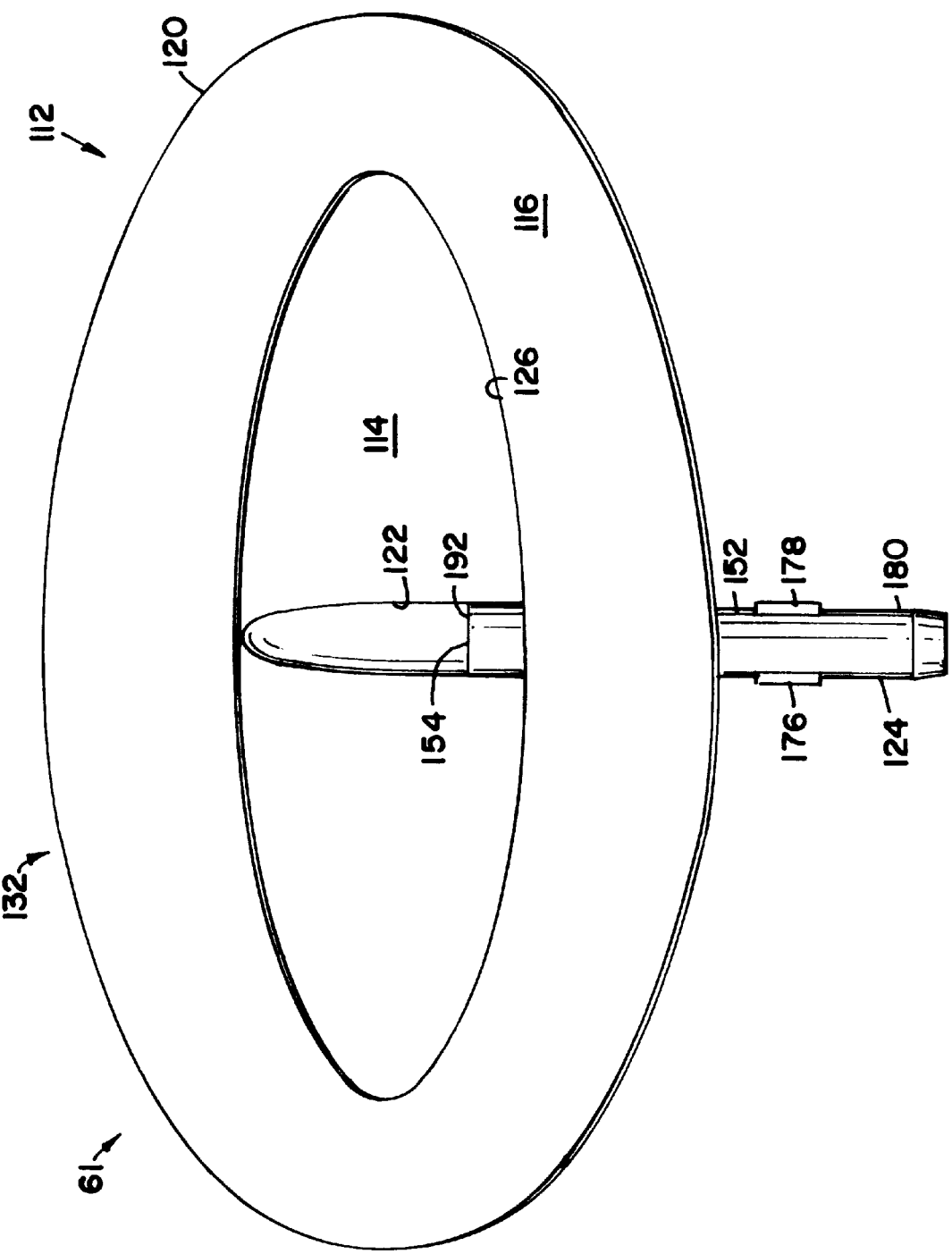

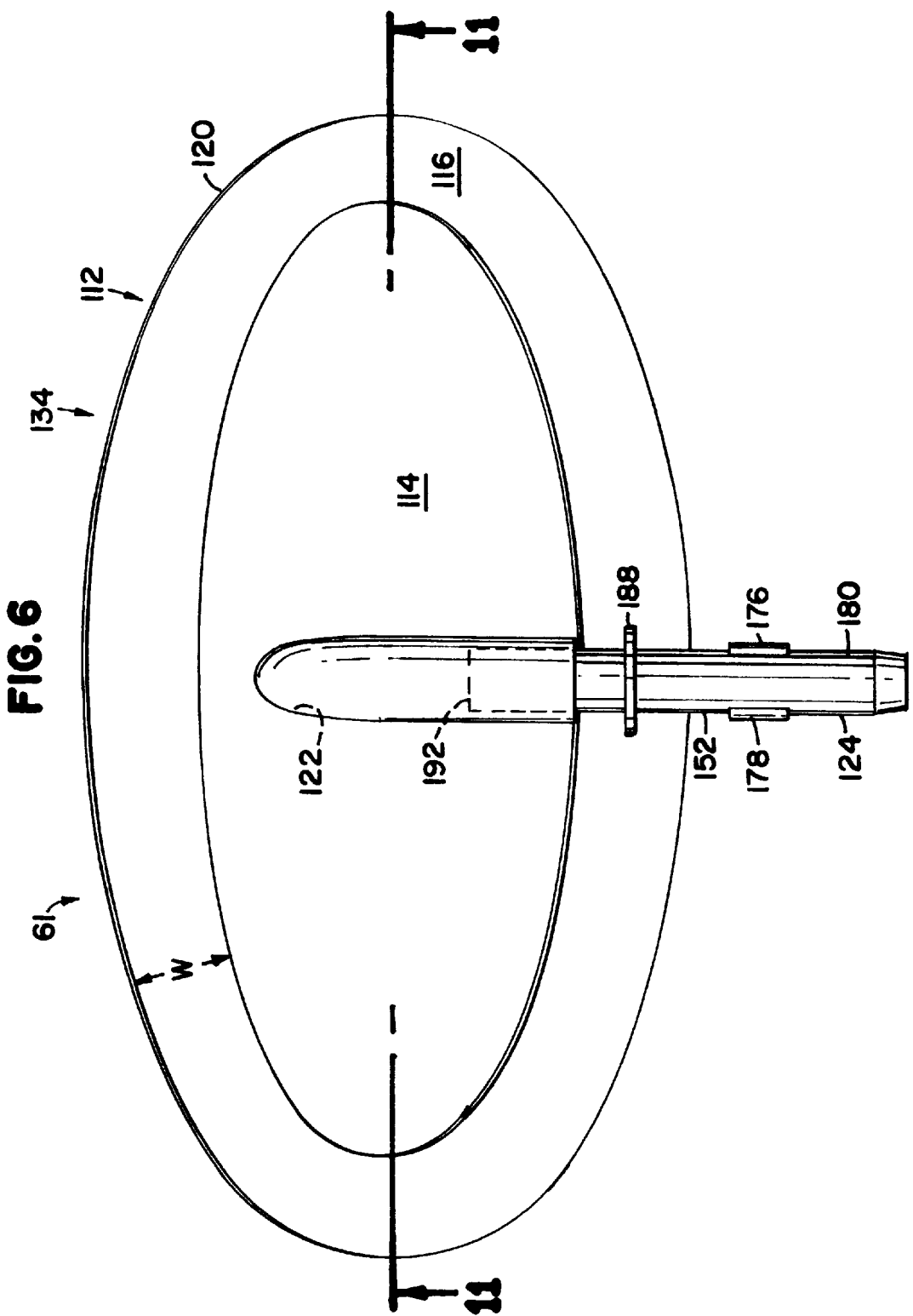

6,142,693

LIQUID DISPENSER AND DISTRIBUTION APPARATUS FOR WASHING STRUCTURES, AND METHODS

FIELD OF THE INVENTION

This disclosure concerns liquid dispenser and distribution constructions. More specifically, this disclosure describes apparatus and methods for dispensing a cleaning solution to wash structures such as vehicles, windows, boats, or other objects.

BACKGROUND OF THE INVENTION

It is desirable to keep the exterior of objects, such as a vehicle, clean. Salt and other contaminants from the environment can cause a vehicle to rust. Various methods have been employed to wash the surfaces of objects. For example, a hose conveying water and a washcloth or brush have been used. Further, a brush attached to an elongated handle has been used. Other types of constructions and methods are also known.

Improvements in apparatus and methods for washing objects such as vehicles or other structures are desirable.

SUMMARY OF THE DISCLOSURE

In one aspect, the disclosure describes a liquid dispenser arrangement including a self-contained pump including a liquid reservoir and a discharge head having an applicator construction and an aperture. The aperture will be in liquid flow communication with the liquid reservoir. The discharge head is constructed and arranged to selectively take in liquid from an external liquid source through the aperture and convey the liquid to the liquid reservoir, when a pressure differential is established between the liquid reservoir and the external liquid source by the pump. The discharge head is also constructed and arranged to selectively eject liquid from the liquid reservoir through the aperture for distribution by the applicator construction.

Preferably, the applicator construction includes a molded, flexible member with the aperture being in a portion of the flexible member. In preferred embodiments, the applicator construction is curved on a radius of about 5–10 inches.

In preferred constructions, the applicator will include a selectively removable mitt covering at least a portion of the member.

Preferred embodiments will include the pump in the form of a tubular member, a plunger slidably received in the tubular member, and a seal member to provide a liquid seal between the tubular member and the plunger.

Preferably, the applicator will include a plurality of regions of differing compliance. Preferably, these regions of differing compliance will allow the applicator to conform to and comply with the surface that is being cleaned.

A method for washing a structure, such as an object like a vehicle, will preferably include constructions and apparatus as described above. In one method, a cleaning solution will be drawn through a porous mitt to fill a reservoir with the cleaning solution. The cleaning solution will be dispensed through the mitt by sliding a plunger into the reservoir.

In another aspect, a discharge head construction is described including a single, integral flexible member having a first section and a second section. The flexible member will have an aperture therethrough, and in preferred embodiments, the first section defines the aperture. Preferably, the second section circumscribes the first section and forms an outer periphery of the flexible member. In preferred embodiments, the second section has a compliance greater than that of the first section.

It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate embodiments of principles of this disclosure and together with the description, serve to explain these principles.

FIG. 2 is an enlarged, partially fragmented, perspective view of the liquid dispenser construction depicted in FIG. 1;

FIG. 3 is an exploded perspective view of the liquid dispenser construction depicted in FIG. 2;

FIG. 5 is an enlarged, top plan view of a discharge head of the liquid dispenser construction depicted in FIG. 2;

FIG. 6 is an enlarged, bottom plan view of the discharge head depicted in FIG. 5;

A. Overview of Operation

Figure 7:
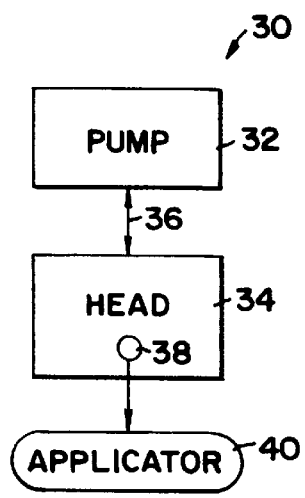
FIG. 7 is a schematic diagram depicting the principles of operation to the liquid dispenser of FIG. 2.

Attention is directed to FIG. 7. FIG. 7 illustrates a schematic diagram depicting overall principles of this disclosure. A liquid dispensing construction is shown in general at 30. The liquid dispensing construction 30 includes a self-contained pump 32 and a discharge head 34. By the term "self-contained", it is meant that the pump is independent of any external mechanisms. That is, the self-contained pump does not have any hoses connected thereto (it is hose-free); nor does it have any power sources such as motors, etc., connected thereto.

The discharge head 34 is in liquid flow communication with the pump 32. This is depicted by arrow 36. The discharge head will include at least a single aperture 38 for permitting the intake and outflow of liquid through the head 34.

In general, the pump 32 induces a vacuum to take liquid in through the aperture 38 of the head 34 to be stored in a reservoir in the pump 32. The pump 32 can then be used to discharge the liquid stored in the reservoir through the discharge head 34 out through the aperture 38.

After the liquid is ejected through the aperture 38, an applicator construction 40 is used to apply and distribute the liquid to a structure, such as the exterior surface of an object such as a car, truck, boat, house, window, etc. Preferably, the pump 32 is configured to also operate as a handle for manipulating the applicator construction 40.

Figure 1:
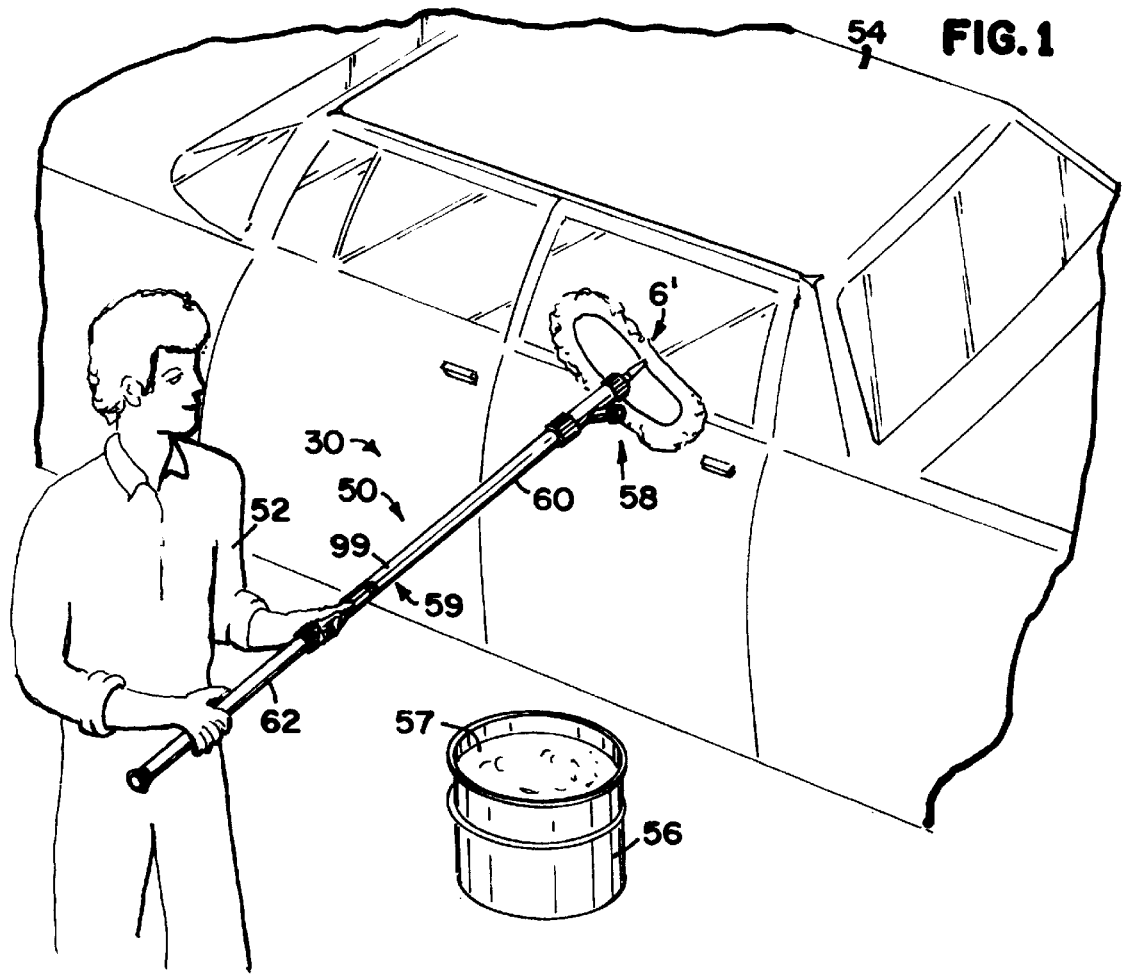
FIG. 1 is a schematic, perspective view illustrating one use of a liquid dispenser construction, according to principles of this disclosure.

Attention is now directed to FIG. 1. FIG. 1 shows schematically, one embodiment and use of the liquid dispenser construction 30. In FIG. 1, a first embodiment of the liquid dispenser construction 30 is illustrated as a liquid dispenser 50. The liquid dispenser 50 is shown in FIG. 1 as being grasped and held by a person 52. The person 52 is using the liquid dispenser 50 to wash or clean an object. In the non-limiting example illustrated in FIG. 1, the object is a vehicle 54. A container 56, such as a bucket, is depicted holding a cleaning solution 57, such as soapy water. It should be understood that other types of solution 57 can be used; for example, liquid wax and other treatments. In general, the person 52 will submerge a discharge head 58 in the container 56, and use a pump 59 to fill a reservoir in the pump 59 with the cleaning solution 57. The person 52 will then press an applicator construction 61 against the structure, such as vehicle 54, and use the pump 32 to discharge or eject the cleaning solution 57 through the discharge head 34 and onto the vehicle 54 (or whatever object is being treated). When the reservoir is either totally or at least partially empty, the person 52 will refill the reservoir and continue to treat or clean the object such as vehicle 54.

A detailed description of each of these parts and assembly follows.

B. The Self-contained Pump 59

Attention is directed to FIG. 2. In FIG. 2, a perspective view of the self-contained pump 59 is depicted. In general, when constructed as shown in the figures, the pump 59 will include a tubular member 60, a plunger 62, and a seal member 64.

The tubular member 60 includes a tubular wall 66 defining a fluid, or liquid, reservoir 68 therein. When constructed as shown in the drawings, the tubular member 66 will be cylindrical with a circular cross-section. The tubular member 66 has a liquid flow channel 70 in liquid flow communication with the liquid reservoir 68 and the discharge head 58, to be described farther below.

Figure 4:
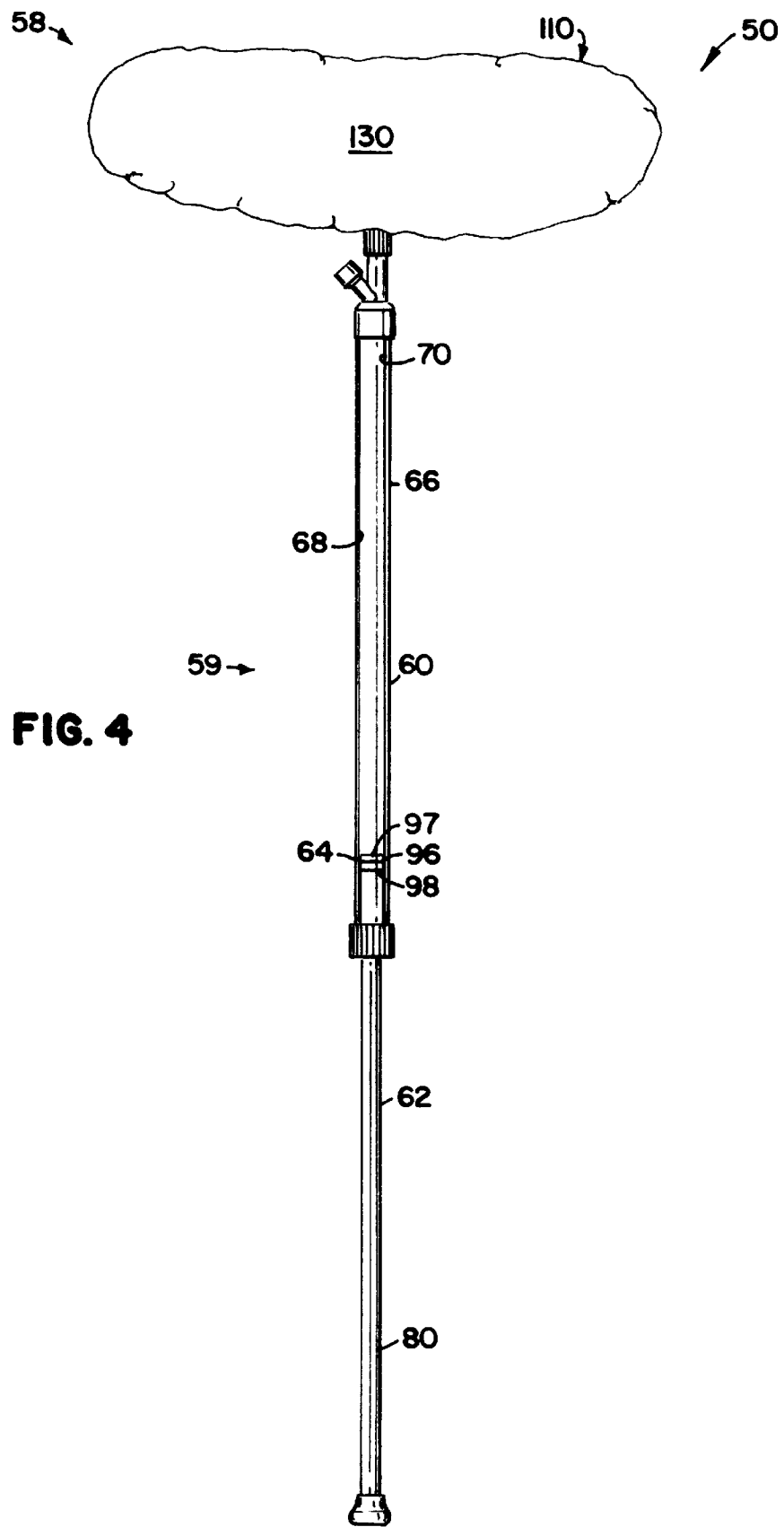
FIG. 4 is a top plan view of the liquid dispenser construction depicted in FIG. 2.

In general, the liquid reservoir 68 will be for holding or containing liquid, such as cleaning solution 57, such as soapy water (or other liquid treatments such as wax), for dispensing through the discharge head 58. The liquid reservoir 68 will change in volume depending upon the position of the plunger 62 within the tubular wall 66. The liquid reservoir 68 will vary between a minimum volume of nothing or almost nothing, when the plunger 62 is fully engaged in the tubular wall 66, and a maximum volume when the plunger 62 is retracted to its fully extended position with respect to the tubular wall 66, as depicted in FIGS. 2 and 4.

Preferably, the maximum volume of the liquid reservoir will be such that, when it is filled with a cleaning solution, the overall liquid dispenser 50 weighs no more than about 5 lbs., preferably no more than 4 lbs. This will provide for easy manipulation by the person 52. Preferably, the maximum volume of the liquid reservoir 68 will be large enough to hold a desirable quantity of cleaning solution to clean a substantial part of the vehicle 54 or other objects before having to refill the reservoir 68. It is contemplated that maximum volumes for the liquid reservoir will be no greater than about 50 ounces, typically about 10–30 ounces, for example 15–20 ounces (preferably about 16–18 ounces), and at least about 5 ounces.

The plunger 62 is slidably received in the tubular member 60. The plunger 62 includes a tubular wall 80 in slidable communication with the tubular member 60. The tubular wall 80 has a seat 82 (FIG. 3) for holding the seal member 64. When constructed as shown in FIGS. 2–4, the tubular wall 80 will be cylindrical having a circular cross-section.

In reference now to FIG. 3, the tubular wall 80 further includes a stop shoulder 84. The stop shoulder 84 is between a first region 86 and a second region 88 having differing diameters. The first region 86 has a larger diameter than the second region 88. The stop shoulder 84 between the first region 86 and second region 88 prevents the plunger 62 from being removed completely from the tubular member 60, and it defines the most retracted position of the plunger 62 relative to the tubular member 60.

The seal member 64 forms a seal 96 between the plunger 62 and the tubular member 60. As can be seen in FIG. 4, the seal member 64 can take the form of first and second O-rings 97, 98 oriented in the seat 82 of the tubular wall 80.

The seal 96 is preferably a liquid seal, such that a pressure differential can be established between the liquid reservoir 68 and an external liquid source, such as the container 56, when the discharge head 58 is submerged in liquid 57 in the container 56.

Attention is now directed again to FIG. 1. By observation of FIG. 1, it can be seen that the self contained pump 59 acts as a handle or extender 99. In particular, the combination of the tubular member 60 and plunger 62 permits the user 52 to reach remote areas or regions of increased height when cleaning. In other words, the tubular member 60 and plunger 62 allow for the positioning of the discharge head 58 on areas such as the roof of a car or other locations on other structures that are normally out of reach of a person.

C. The Discharge Head 58

Figure 8:
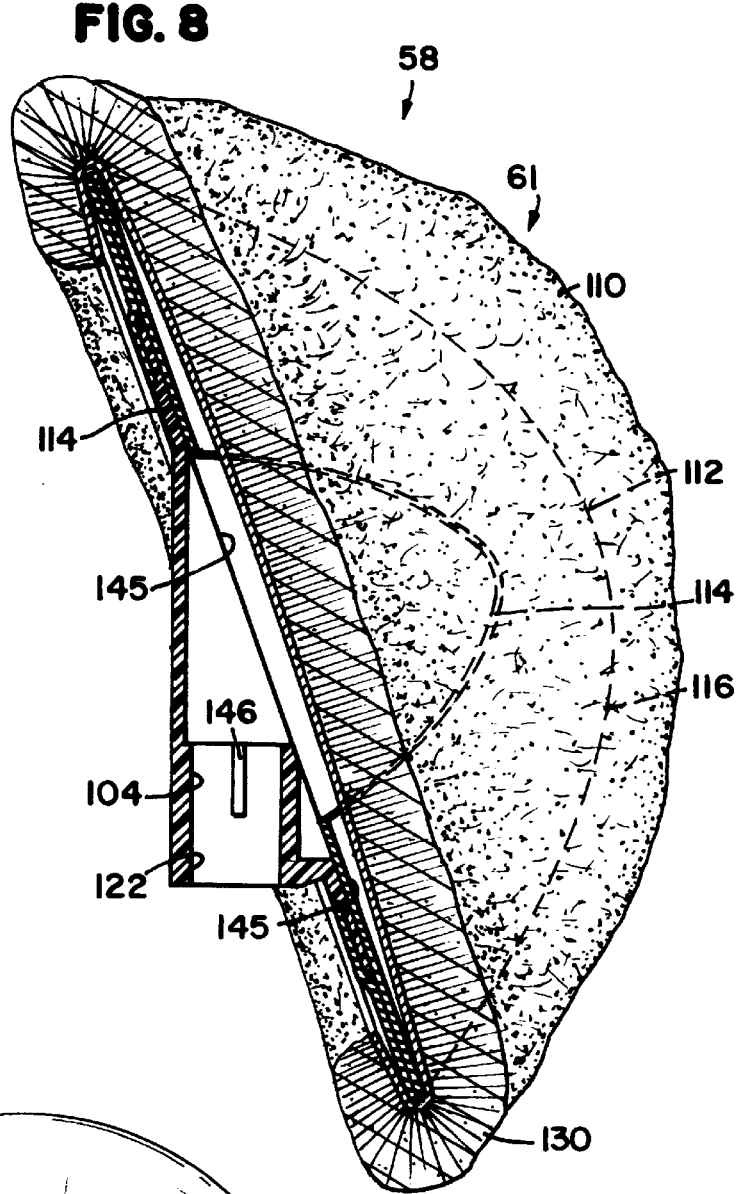
FIG. 8 is a cross-sectional, perspective view of the discharge head, taken along the line 8—8 of FIG. 3.

In preferred constructions, the liquid dispenser 50 will include discharge head 58. The discharge head 58 will preferably operate to take in, such as by suction, liquid and then expel or eject the liquid. Preferably, the discharge head 58 will be in liquid flow communication with the liquid reservoir 68 and include a passageway for communication with the reservoir 68. In preferred constructions, the discharge head 58 will include at least a single aperture 104 (FIG. 8). In other embodiments, there may be multiple apertures.

Preferably, the discharge head 58 includes applicator construction 61. The applicator construction 61 functions to distribute the liquid 57 stored in the liquid reservoir 68. The applicator construction 61 includes applicator media 110 for distributing the liquid.

While a variety of embodiments are contemplated herein, in preferred applications, the applicator construction 61 will comprise a flexible member 112 (FIG. 5) with the aperture 104 being in a portion of the member 112. Preferred implementations will include the aperture 104 in approximately a geometric center of the flexible member 112. The flexible member 112 will include preferably at least a first region 114 of flexibility and a second region 116 of flexibility. Preferably, both the first region 114 and second region 116 are part of a single, integral construction.

The first region 114 will provide structural integrity. The first section 114 will provide stiffness for ease of handling and manipulation of the discharge head 58. Preferred constructions will include the first region 114 being constructed of a material that is less compliant than the second region 116. By the term "compliant" or "compliance", it is meant the displacement of the first region 114 or second region 116 under a unit of force. When the first region 114 is "less compliant" than the second region 116, it means that first region 114 will have a smaller displacement than the second region 116, given the same unit of force on each of the first region 114 and second region 116.

The second region 116 acts to provide increased contact with the surface to be washed. Preferably, the second region 116 accomplishes this by providing flexibility to applicator construction 61. The second region 116, in preferred constructions, will be more compliant than the first section 114.

The first region 114 and second region 116 are preferably arranged to provide for convenient handling and manipulation of the overall liquid dispenser 50. While a variety of embodiments are contemplated herein, in the particular embodiments illustrated in FIGS. 5 and 6, the second region 116 will define an outer periphery 120 of the flexible member 112. When constructed as shown in FIGS. 5 and 6, the second region 116 circumscribes or surrounds the first region 114. Note that the first region 114 defines a groove or channel 122. The channel 122, in preferred constructions, acts to receive structure, such as a stem 124 to convey liquid between the discharge head 58 and the liquid reservoir 68. The channel 122 preferably defines the aperture 104 for the liquid flow communication between the reservoir 68 and the discharge head 58. Preferably, the channel 122 is located in a geometric center of both the first region 114 and the second region 1 16.

The first region 114 and second region 116 can have a variety of shapes. In the particular embodiment illustrated, the first region 114 has a non-circular, and generally elliptical or oval shape, while the second region 116 also has an elliptical or oval shape, but defines a nonsolid center 126. The inner dimension of the nonsolid center 126 is preferably smaller than the outermost dimension of the first region 114. In this way, there is an overlap 123 (FIG. 11) between the first region 114 and second region 116, permitting the second region 116 to circumscribe the first region 114. In other embodiments the first region 114 and second region 116 can be "racetrack" shaped (semi-circular ends joined by straight segments), rectangularly shaped, circular, or irregularly shaped, for example.

Figure 11:
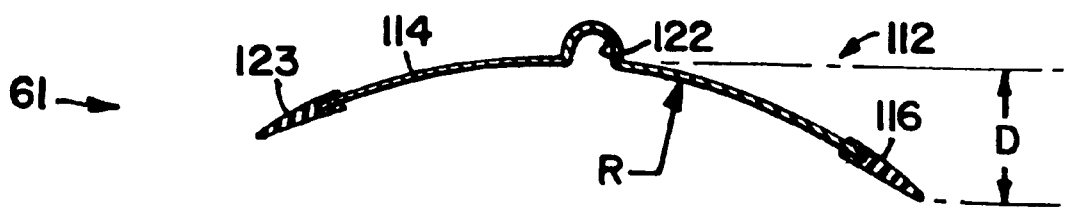
FIG. 11 is a reduced cross-sectional view of the discharge head taken along the line 11—11 of FIG. 6.

As can be seen in FIGS. 2, 3, and 11, preferably the applicator construction 61 is non-flat. In other words, in preferred embodiments, the first region 114 and second region 116 do not completely lie in a single plane. In more preferred embodiments, the applicator construction 61 is convex or curved. The curving of the applicator construction 61, in combination with the difference in compliance between the first region 114 and second region 116, contributes to a liquid dispenser 50 that is convenient and easy handle and manipulate. Further, the curved construction of the applicator construction 61 helps to form a pocket or air space between the media 110 and the flexible member 112. This is explained further below. In preferred constructions, the applicator construction is curved on a radius R (FIG. 11) of at least 4 in., typically about 5–10 in., for example about 6–9 in., and no greater than about 15 in.

The convex or curved applicator construction 61 helps the applicator construction conform to non-flat surfaces. In particular, the applicator construction 61, having the curved shape to it, is better able to clean irregular shapes, contours, and corners. When working flat surfaces, the applicator construction 61 has sufficient flexibility to flatten with light pressure (that is, pressure under 10 lbs. of force) for cleaning the flat surfaces. In particular, the second region 116 has a flexibility and compliance that permits the second region 116 to bend and conform relative to the surface that it is pressed against to be cleaned. In preferred embodiments, the applicator construction 61 will flatten at hand pressures of 6–9 lbs. of force, for example, about 8.5 lbs. of force when a mitt 130 is dry. When mitt 130 is saturated with liquid, the applicator construction 61 will flatten at hand pressures of 4–8 lbs. of force, for example, about 6.5 lbs. of force. By "flatten", it is meant that the radius of curvature R (FIG. 11) will be nothing such that the applicator construction 61 is straight, planar, or flat; however, a complete flattening is not required (that is, the radius R can become very large, on the order of greater than 25 inches).

Although the applicator construction 61 has advantages due to its shape, it should be appreciated that the applicator construction 61 can be formed in a variety of shapes and configurations and achieve the same advantages. However, the particular applicator construction 61 depicted in the drawings is preferred. The preferred applicator construction 61 depicted in the drawings is distinctive to the applicant, attractive, and eye-catching in appearance.

As mentioned above, preferred applicator constructions 61 will include distribution media 110 for helping to distribute and apply the cleaning solution 57 to the desired object. In the particular embodiments illustrated in the drawings, the media 110 includes a selectively removeable mitt 130 covering at least a portion of the flexible member 112. The mitt 130, in preferred embodiments, is oriented around the outer periphery 120 of the second region 116. Preferably, the mitt 130 will cover the entire application face 132 (FIG. 5), and only cover a partial amount of the connector face 134 (FIG. 6). Attention is directed to FIGS. 2–4. In FIG. 4, it can be seen that the mitt 130 is covering the entire application face 132. On the opposite side, shown in FIGS. 2 and 3, the mitt 130 is surrounding the periphery 120, wrapping over the ends, and generally covering the second region 116, leaving the first region 114 exposed. This permits access between the pump 59 and the discharge head 58, without undue interference by the mitt 130.

In preferred applications, the mitt 130 is selectively removeable and replaceable from the flexible member 112. This permits the mitt 130 to be replaced when it is soiled. Alternatively, the mitt 130 can be removed from the flexible member 112 and then cleaned. After cleaning, the mitt 130 can be replaced on the flexible member 112. Preferably, the mitt 130 will include structure to secure the mitt 130 to the flexible member 112. This may be accomplished by elastic 136 around the periphery 140 of the mitt 130. The elastic 136 permits stretching of the mitt 130 around the flexible member 112 for change out. Alternatively, the mitt 130 can include tethers or tie strings securing the mitt 130 to the flexible member 112.

In preferred applications, the mitt 130, after mounting on the flexible member 112 will be spaced, at least in certain regions from the surfaces of at least the first region 114 and in many instances, portions of the second region 116, on the application face 132. This spacing creates an open volume or air pocket 145 (FIG. 8) between the mitt 130 and the flexible member 112. The air pocket 145 helps create a passive pump. That is, when pressing the applicator construction 61 against the surface to be cleaned, the mitt 130 will press against the aperture 104 to close the air space 145. When pressure between the applicator construction 61 and the surface to be cleaned is relieved, the pocket 145 between the mitt 130 and the flexible member 132 will decrease in pressure and pull liquid from the liquid reservoir 68 into the volume of air space 145. In this manner, the liquid will flow from the liquid reservoir 68 through the aperture 104 and through the mitt 130 for distribution, without effort of depressing the plunger 62 in the tube 60. It is foreseen, however, that in regions of particularly dirty areas, the plunger 62 can be depressed into the tubular member 60 to provide an extra burst of liquid pressure from the reservoir 68 through the mitt 130.

It should be noted that the mitt 130 is generally self-cleaning. The cleaning solution 57 is distributed by the mitt 130, and helps to keep the mitt 130 clean over long periods of time. Eventually, however, it is foreseen that the mitt 130 will need to be removed from the flexible member 112 and either replaced with a new mitt 130; or alternatively, cleaned and then remounted on the flexible member 112.

Figure 10:
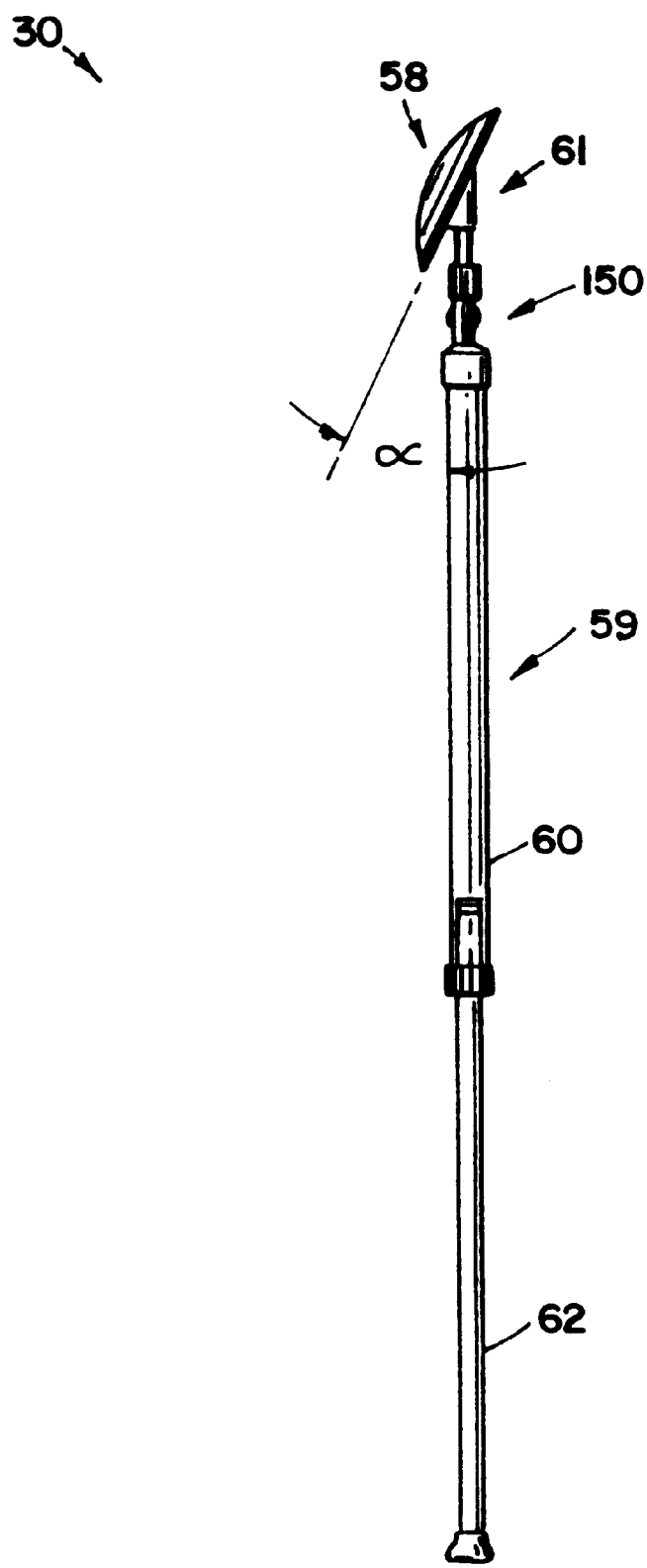
FIG. 10 is a side elevational view of the embodiment of the liquid dispenser construction depicted in FIG. 2 and without a mitt covering the discharged head.

In preferred constructions, the discharge head 58 is angled relative to the pump 59. The angle between the discharge head 58 and the pump 59 helps to contribute to better handling and manipulation of the overall liquid dispenser. Attention is directed to FIG. 10. Preferably, the angle a between the discharge head 58 and the pump 59 is at least about 5°, no greater than about 70°, typically about 10–50°, for example about 15–25°, (and in the specific embodiment illustrated, about 18–20°).

D. Connector Assembly 150

Attention is directed to FIG. 3. A connector assembly 150 provides connection between the discharge head 58 and the pump 59. One particularly preferred, convenient connector assembly is illustrated in FIG. 3.

FIG. 3 is an exploded, perspective view of the liquid dispenser 50. The connector assembly 150 shown includes stem 124 for providing a liquid conduit between the aperture 104 and the liquid flow channel 70 in the tubular member 60. Preferably, the stem 124 is a tubular member 152 with a channel 154 running the length of the tubular member 152.

The preferred connector assembly 150 also includes a threaded nut 158 and an end cap construction 160. The end cap construction 160 includes a cup 162 secured to the end of the tubular member 60 of the pump 59. The cup 162 preferably has a circular cross section and is generally cylindrical in shape. Integral with the cup 162 is a generally cylindrical extension 164 with a side branch 166. The side branch 166 is plugged with plug member 168. In alternate applications, the plug member 168 can be unplugged and connected for fluid flow communication with a hose or a conduit.

At the end of extension 164 is a threaded neck 170. The neck 170 is constructed and arranged for receipt of the tubular member 152. In general, the end cap construction 160 has a hollow channel for conveying liquid from the liquid reservoir 68 to the channel 154 in the stem 124.

Figure 9:
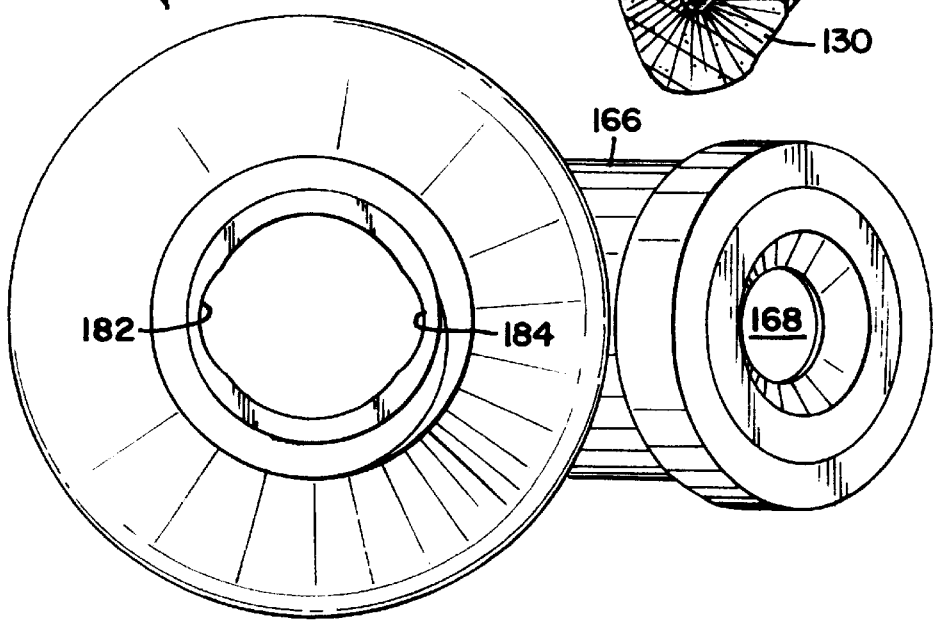
FIG. 9 is an end view of the end cap construction depicted in FIG. 3 and taken along the line 9—9.

Preferably, the connector assembly 150 includes structure for preventing rotation of the discharge head 58 relative to the pump 59. In the preferred embodiment, the tubular member 152 includes a plurality of projections 176, 178 extending from or projecting from the wall 180 of the tubular member 152. The projections 176, 178 rest in recesses 182, 184 (FIG. 9) of the neck 170. When operably assembled, the projections 176, 178 mounted in the recesses 182, 184 will prevent rotation of the discharge head 58 relative to the pump 59.

In reference now to FIG. 6, note that the tubular member 152 also includes a projecting flange 188. When the stem 124 is locked in place between the end cap construction 160 and the discharge head 58, the flange 188 provides a lock or stop against an associated stop surface in the nut 158. In this way, when the threaded nut 158 is engaged against the threaded section 190 in the neck 170, the stem 124 will be locked into the end cap construction 160. That is, the flange 188 prevents the stem 124 from sliding out through the nut 158.

Attention is directed to FIGS. 5 and 6. The stem 124 slideably engages the groove or channel 122. That is, the stem 124 has an insertion end 192 that slides in the channel 122. Preferred implementations include flanges projecting radially from the stem 124 to slidingly engage slots 146 (FIG. 8). This structure helps to keep the flexible member 112 from rotating relative to the connector assembly 150. The channel 154 of the stem 124 permits the flow of liquid from the liquid reservoir 68 into the volume between the mitt 130 and the flexible member 112 for distribution by the mitt 130.

E. Example Operation

In operation, the user 52 will push the plunger 62 at least partially or fully to the end 75 of the tubular member 60. The user 52 will then submerge the discharge head 58 into liquid, such as cleaning solution 57. The user 52 will move the plunger 62 away from the end 75 to create a pressure differential between the liquid reservoir 70 and the source of liquid. As the plunger 62 is pulled away from the discharge head 58, the liquid is drawn through the porous mitt 130. The liquid then flows into the channel 122. From there, the liquid flows into the liquid reservoir 68. It flows from the channel 122 into the liquid reservoir 68 by passing through the channel 154 in the stem 124, and then through the open channel in the end cap construction 160.

The liquid, such as cleaning solution 57, is then dispensed through the mitt 130. This step may be done by sliding the plunger 62 into the reservoir 68 and toward the discharge head 58. This may also include pressing the mitt 130 against the surface to be cleaned, such as vehicle 54, by holding the pump 59. As the mitt 130 is pressed against the surface to be cleaned, the mitt 130 will press against the aperture 104 to close the air pocket 145. When the pressure between the applicator construction 61 and the surface to be cleaned is relieved, the pocket 145 will increase in volume and decrease in pressure. This decrease in pressure pulls liquid from the liquid reservoir 68 into the pocket 145, thereby acting as a passive pump.

The liquid will drain from the reservoir 68. After at least a portion of the reservoir 68 is emptied of the cleaning solution 57, the reservoir 68 will be refilled. This may be done by submerging the mitt 130 and discharge head 58 again into the cleaning solution 57. The plunger 62 will be pulled by the user in a direction away from the discharge head 58 to expand the volume in the liquid reservoir 68. This will draw the cleaning solution 57 through the mitt 130, through the aperture 104 and into the reservoir 68.

These steps are repeated until the vehicle 54 (or whatever surface is being cleaned) is cleaned to the person's desire.

After a period of use, it may become desirable to replace the mitt 130. The mitt 130 can become soiled after extended periods of use, or quicker if cleaning a particularly dirty structure. The user 52 will grasp the mitt 130 and remove it from the flexible member 112. This can be done by either untying the mitt 130; or alternatively, stretching the mitt 130 from around the outer periphery 120 of the flexible member 112. The old, soiled mitt can then be disposed of. Alternatively, the old mitt 130 can be cleaned. The cleaned mitt or replacement mitt 130 is then again secured to the flexible member 112. This can be done by stretching the mitt 130 to fit around the periphery 120. Alternatively, the mitt 130 is fitted around the periphery 120 to cover the applicator face 132, and the mitt 130 is secured to the flexible member 112. One example of securing the mitt 130 to the flexible member 112 is done by tying with strings or other tethers.

F. Example Materials and Dimensions

Described below are example dimensions and materials for specific embodiments. Of course, a wide variety materials and dimensions are useable.

Preferably, the first region 114 of the flexible member 112 is constructed of plastic. One useable plastic is polypropylene. One example polypropylene is commercially available from FINA under product number 3622. This material has a hardness of about 64, Shore D; 92, Rockwell R. It has a tensile strength of about 5,100 psi (35 M Pa); an elongation of about 8%; a tensile modulus of about 250,000 psi (1,730 M Pa); a flexural modulus of about 230,000 psi (1,585 M Pa); an Izod impact at 73° F. of 0.4 ft lbs./in. notched (21.0 J/m), and 18.0 ft lbs. unnotched (955 J/m); and a heat deflection at 66 psi of 230° F. (110° C. at 4.84 (kg/cm$^2$).

Preferably, the second region 116 is constructed of a material of greater compliance than the first region 114. The second section 116 can be constructed of a material that provides more flexibility than the first region 114. For example, the second region 116 can be constructed of rubber or thermoplastic rubber. One useable material is a thermoplastic, such as Santoprene® thermoplastic rubber 121-73 W 175, available from Advanced Elastomer Systems of Akron, Ohio. This material has a hardness of no greater than 85 Shore A, typically between 65–80 Shore A (inclusive), for example, typically 70–75 Shore A, and in one example, 73 Shore A; a specific gravity of 0.97; a tensile strength of about 1200 psi (8.3 M Pa); an elongation of 440%; and a 100% modulus of 520 psi (3.6 M Pa).

Preferably, the stem 124 is constructed of hard plastic or nylon. One usable material is nylon 6/6, unfilled, available from Emtec Engineered Resins under product number N1000EL. The nut 158 is also preferably constructed of a non-metal material, such a polypropylene. One usable material is commercially available from Spartech Polycom under product number PP5410 A1. Each of the materials of the connector assembly 150 is preferably non-metal, to prevent rusting.

The mitt 130 is preferably constructed of a porous material. The mitt 130 can be cloth, with cotton or polyester projecting fuz. In alternate constructions, the mitt 130 can be foam. The mitt 130 can be other materials that absorb and distribute liquid easily and conveniently, such as a mop with a plurality of extending elongate strands.

The pump 59 is preferably constructed of plastic.

In one embodiment, the plunger will preferably have a length of at least 10 in., typically 15–30 in., for example 22–26 in., and not greater than about 3 ft. The tubular member 60 will preferably have a length of at least about 10 in., and no greater than about 35 in., typically about 15–30 in., for example about 22–26 in. The tubular member 60 will have a diameter of at least about 0.5 in., no greater than about 3 in., typically 1–2 in., for example about 1.2–1.8 in.

The preferred applicator construction 61 will have an overall greatest outermost dimension (major dimension) of at least about 5 in., no greater than about 15 in., typically about 6–12 in., for example about 8–10 in. Preferably, the application face 132 will have a surface area (the area defined by the outer periphery 120) of at least about 10 sq. in., no greater than about 100 sq. in., typically about 20–70 sq. in., for example about 30–50 sq. in. It will preferably have a minor dimension of at least about 0.5 in., no greater than about 10 in., typically 2–8 in., for example about 3–6 in. Preferably, it will have a depth D (FIG. 11) of at least about 0.25 in., no greater than about 5 in., typically about 0.5–3 in., for example about 1–2 in. In preferred arrangements, the second region 116 will have a perimeter width W (FIG. 6) of at least about 0.25 in., no greater than 5 in., typically 0.5–4 in., for example 1–3 in.

It should be appreciated that the liquid dispensing construction 30 can be implemented in a variety of shapes and configurations. The particular embodiment illustrated in the drawings is preferred. The particular embodiment illustrated in the drawings is distinctive, eye-catching, and attractive in appearance. Additional views of the liquid dispensing construction 30 are depicted in co-pending and commonly assigned U.S. patent Ser. No. 29/105744, filed the same date herewith, and entitled, "Dispensing and Washing Apparatus," herein incorporated by reference.

The above specification, examples and data provide a complete description of the manufacture and use of the invention. Many embodiments of the invention can be made according to the disclosed principles.

We claim:

1. A liquid dispenser arrangement comprising:
   (a) a self-contained pump including a liquid reservoir;
   (b) a discharge head having an applicator construction and an aperture; said aperture being in liquid flow communication with said liquid reservoir;
      (i) said applicator construction comprising a flexible member having an application face; said flexible member having a first flexible section and a second flexible section;
         (A) said application face having a surface area of at least 10 square inches;
         (B) said first flexible section being constructed of a different material than a material of said second flexible section;
         (C) said first flexible section and said second flexible section being part of a single, integral construction;
         (D) said second flexible section having a compliance greater than that of said first flexible section;
         (E) said applicator construction being curved on a radius of at least 4 inches and no greater than 15 inches;
      (ii) said discharge head being constructed and arranged to selectively take in liquid from an external liquid source through said aperture and convey the liquid to said liquid reservoir, when a pressure differential is established between said liquid reservoir and the external liquid source by said pump; and
      (iii) said discharge head being constructed and arranged to selectively eject liquid from said liquid reservoir through said aperture for distribution by said applicator construction.

2. A liquid dispenser arrangement according to claim 1 wherein:
   (a) said discharge head is oriented relative to said pump at an angle between 10–50°.

3. A liquid dispenser arrangement according to claim 1 wherein:
   (a) said flexible member comprises a molded construction with said aperture being in a portion of said member.

4. A liquid dispenser arrangement according to claim 3 further including:
   (a) a tube providing liquid flow communication between said liquid reservoir and said aperture in said discharge head;
      (i) said tube having at least a single projection to prevent rotation of said discharge head relative to said pump.

5. A liquid dispenser arrangement according to claim 3 wherein:

(a) said applicator construction further includes a selectively removable mitt covering at least a portion of said member.

6. A liquid dispenser arrangement according to claim 5 wherein:
   (a) said mitt is oriented to cover said aperture;
       (i) said mitt including an inner surface spaced from said aperture to form a volume therebetween;
       (ii) said flexible member being constructed and arranged to change a size of said volume to draw liquid from said liquid reservoir and into said volume.

7. A liquid dispenser arrangement according to claim 1 wherein:
   (a) said second flexible section defines an outer periphery of said member;
       (i) said second flexible section circumscribing said first flexible section;
       (ii) said first flexible section defining said aperture; said aperture being in about a center of said member.

8. A liquid dispenser arrangement according to claim 7 wherein:
   (a) said second flexible section has a hardness no greater than 85 Shore A.

9. A liquid dispenser arrangement according to claim 7 wherein:
   (a) said pump comprises:
       (i) a first tubular member defining said liquid flow reservoir and having a liquid flow channel;
           (A) said liquid flow channel being in fluid communication with said aperture in said discharge head;
       (ii) a plunger slidably received in said first tubular member; and
       (iii) a seal member constructed and arranged to provide a liquid seal between said first tubular member and said plunger.

10. A liquid dispenser arrangement according to claim 9 wherein:
    (a) said liquid flow reservoir has a maximum volume of no greater than 50 ounces; and
    (b) the surface area of said application face is no greater than 100 square inches.

11. A liquid dispenser arrangement according to claim 1 wherein:
    (a) said discharge head is oriented relative to said pump at an angle of no greater than 70°.

12. A method for washing an object comprising:
    (a) drawing a cleaning solution through a discharge head including a flexible member covered by a porous mitt to fill a reservoir with the cleaning solution;
        (i) the porous mitt being spaced from portions of the flexible member to define an air pocket with a volume therebetween;
    (b) pressing the flexible member against the object to press the mitt against the flexible member to decrease the pocket volume; and
    (c) relieving pressure between the flexible member and the object to: (i) increase the pocket volume; (ii) decrease pressure in the pocket; and (iii) pull cleaning solution from the reservoir into the pocket.

13. A method for washing an object according to claim 12 further including:
    (a) after at least a portion of the reservoir is emptied of the cleaning solution, refilling the reservoir by submerging the discharge head in the cleaning solution, pulling the plunger to expand a volume of the reservoir, and drawing the cleaning solution through the mitt and into the reservoir.

14. A discharge head construction comprising:
    (a) a single, integral flexible member having an aperture, a first section, and a second section;
        (i) said second section circumscribing said first section and forming an outer periphery of said flexible member;
            (A) said second section comprising thermoplastic rubber;
            (B) said second section having a hardness no greater than 85 Shore A;
            (C) said first section comprising plastic;
        (ii) said second section having a compliance greater than that of said first section; and
        (iii) said first and second sections being curved on a radius of about 5–10 in.

15. A discharge head construction according to claim 14 wherein:
    (a) said second section has a hardness of 70–75, Shore A; and
    (b) said first section comprises polypropylene.

16. A discharge head construction according to claim 15 further comprising:
    (a) a selectively removable mitt oriented to cover said aperture; and
    (b) said first section defines said aperture.

17. A discharge head construction according to claim 14 wherein:
    (a) said flexible member is non-circular in shape; and
    (b) said flexible member includes an application face having a surface area of about 20–70 square inches.

18. A discharge head construction according to claim 14 wherein:
    (a) said second section has a perimeter width of about 0.5–4 inches.

* * * * *